US00PP17235P3

(12) United States Plant Patent
Hanes

(10) Patent No.: US PP17,235 P3
(45) Date of Patent: Nov. 28, 2006

(54) ***PELARGONIUM* PLANT NAMED 'CLIPS LITSALTWO'**

(50) Latin Name: *Pelargonium×hortorum*
Varietal Denomination: Clips Litsaltwo

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 186 days.

(21) Appl. No.: 11/091,202

(22) Filed: Mar. 28, 2005

(65) Prior Publication Data

US 2006/0218685 P1 Sep. 28, 2006

(51) Int. Cl.
*A01H 5/00* (2006.01)

(52) U.S. Cl. ..... Plt./327
(58) Field of Classification Search ..... Plt./327
See application file for complete search history.

*Primary Examiner*—Kent Bell
(74) *Attorney, Agent, or Firm*—Jondle & Associates P.C.

(57) ABSTRACT

A *Pelargonium* cultivar particularly distinguished by its light salmon flower color and dark green leaves is disclosed.

1 Drawing Sheet

Figure 1:
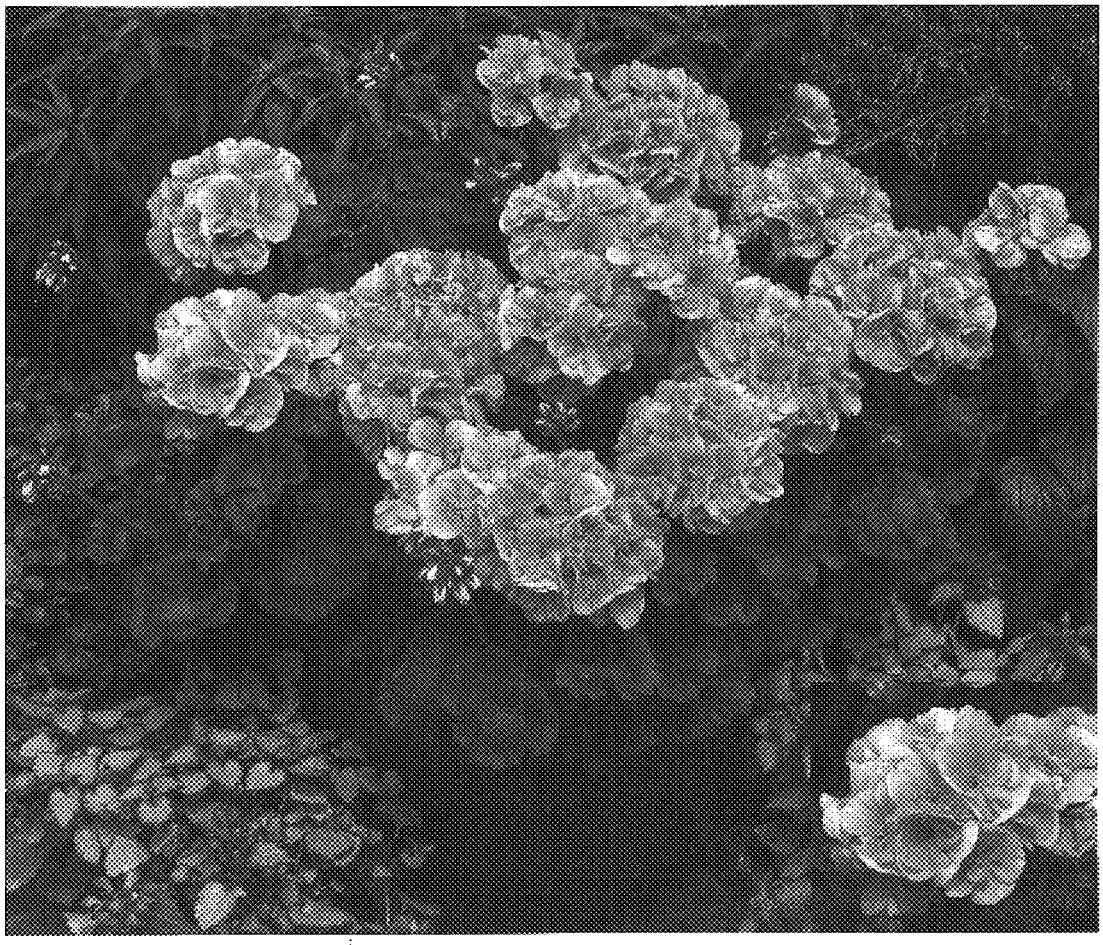

Genus and species: *Pelargonium×hortorum* L.H. Bailey. Variety denomination: 'Clips Litsaltwo'.

BACKGROUND OF THE NEW PLANT

The present invention comprises a new and distinct cultivar of *Pelargonium*, botanically known as *Pelargonium× hortorum* L.H. Bailey, and hereinafter referred to by the cultivar name 'Clips Litsaltwo'. The new cultivar was propagated from a seedling resulting from the cross of 7886-1, a red-flowered, unnamed and unpatented proprietary *Pelargonium* line, as the female parent, and 'Champion', an orange-flowered *Pelargonium*, as the male parent.

The new cultivar was created in 1998 in Gilroy, Calif. and has been asexually reproduced repeatedly by cuttings in Gilroy, Calif. over a five-year period. It has also been trialed at Gilroy, Calif., Litchfield, Mich., and Andijk, The Netherlands. It has been found to retain its distinctive characteristics through successive asexual propagations. 'Clips Litsaltwo' reproduces true to type through successive generations of asexual reproduction.

DESCRIPTION OF PHOTOGRAPH

This new geranium plant is illustrated by the accompanying photograph which shows blooms, buds, and foliage of the plant; the colors shown are as true as can be reasonably obtained by conventional photographic procedures. The photograph is of a 4–5 months-old plant grown in a lexan-covered greenhouse with other zonal *pelargonium* culture.

FIG. 1. shows overall plant habit while the inset photograph shows a closer view of the mature inflorescence.

DESCRIPTION OF THE NEW CULTIVAR

The following detailed descriptions set forth the distinctive characteristics of 'Clips Litsaltwo'. The data which defines these characteristics were collected from asexual reproductions carried out in Gilroy, Calif. The plant history was taken on seven-month-old plants grown in 1 gallon pots in a poly-covered greenhouse during the fall/winter season.

The color readings were taken under natural light in the greenhouse in the late winter season. Color references are primarily to The R.H.S. Colour Chart of The Royal Horticultural Society of London (R.H.S.) (2001). Texture description data were collected by viewing plant parts with a dissecting microscope.

DETAILED BOTANICAL DESCRIPTION

Classification:
- *Botanical.*—*Pelargonium×hortorum* L.H. Bailey.
- *Common name.*—Geranium.

Growth:
- *Form.*—Upright, outwardly spreading and rounded growth habit.
- *Growth and branching habit.*—Good vigorous habit, well branched.
- *Height.*—20–25 cm as measured from soil level to top of plant, excluding blooms; 30–40 cm from soil level to top of umbels.
- *Width.*—50–55 cm excluding umbels.
- *Time to produce a finished flowering plant.*—8–10 weeks.
- *Outdoor plant performance.*—Has good weather tolerance; used in hanging baskets, patio or mixed containers.
- *Time to initiate and develop roots.*—12–28 days.
- *Root description.*—White, slightly pubescent, fibrous yet coarse.

Leaves:
- *Arrangement.*—Alternate, simple.
- *Apex description.*—Acute.
- *Base description.*—Cordate.
- *Shape.*—Orbicular.
- *Margin.*—Slightly denticulate.
- *Texture.*—Pilose; few glandular hairs.
- *Venation.*—Palmate.
- *Venation color.*—RHS 144B.
- *Immature leaf.*—Color: Upper surface: RHS 147A. Lower surface: RHS 147B. Length: 3.4–4.0 cm. Width: 5.5–6.5 cm.

*Mature leaf.*—Color: Upper surface: RHS147A. Lower surface: RHS 147B. Length: 4.0–4.5 cm. Width: 7.5–7.9 cm.
*Zonation color.*—RHS 200A but lighter.
*Zonation diameter.*—1.0 cm.
*Petioles.*—Length: 4.0–5.0 cm. Diameter: 0.3 cm. Color: Between RHS 144A and RHS 144B. Texture: Hirsute; pilose; few glandular hairs.

Stems:
*Length.*—35–40 cm.
*Internode length.*—1.5–2.0 cm.
*Color.*—RHS 146A with some irregular blotches of anthocyanin on upper surface.
*Texture.*—Pilose; many glandular hairs.

Flower buds:
*Diameter.*—0.7–0.9 cm.
*Length.*—1.0 cm.
*Shape.*—Elliptical.
*Color when sepals first divide.*—RHS 27B with very faint blush of RHS 39B.

Inflorescence:
*Type.*—An umbel composed of 18–22 flowers.
*Umbel diameter.*—9.0–9.5 cm.
*Umbel depth (height).*—6.0–7.0 cm.
*Blooming habit.*—Continuous blooming throughout the growing season; good floriferousness.
*Peduncle.*—Length: 12–16 cm. Diameter: 0.4 cm. Texture: Pilose; many glandular hairs. Color: RHS 144A with slight coloring of anthocyanin in irregular blotches.
*Pedicel.*—Length: 0.8–1.0 cm. Diameter: 0.1 cm. Texture: Many glandular hairs, some with an orange hue. Color: RHS 144A with anthocyanin in irregular blotches.

Flowers:
*Flower form.*—Polypetalous; mostly imbricate petals and petaloids, semi-double form consisting of 5 petals and 4 petaloids.
*Flower diameter.*—3.5–4.3 cm.
*Flower persistence.*—An open flower will hold its petals until the flower begins to dehisce, 7–10 days.
*Fragrance.*—None.

Petals/petaloids:
*Petal size.*—Length: 2.1–2.3 cm. Width: 2.1–2.3 cm.
*Shape.*—Obovate.
*Apex.*—Rounded.
*Base.*—Acute.
*Margin.*—Entire.
*Texture.*—Papillose.
*Upper petal color.*—Upper surface: RHS N155B but whiter, blushed faintly with RHS 49A; vein color of RHS 52B. Lower surface: RHS 49A with faint streaks of RHS 43C.
*Lower petal color.*—Upper surface: RHS N155B but whiter; blushed with 49A; faint veining of RHS 52B. Lower surface: RHS 49A with slight streaks of RHS 43C.
*Upper petaloid color.*—Upper surface: RHS N155B but whiter with a blushing between RHS 49A and RHS 50C; faint veining and streaking of RHS 52B.
*Lower petaloid color.*—Upper surface: RHS N155B but whiter, with a blushing of RHS 49A and 50C; vein color of RHS 52B.
*Color change with age.*—Colors do not change with age but may change with temperature and time of year.

Sepals:
*Number of sepals.*—5, one larger than the others; fused at base.
*Length of sepals.*—0.8–0.9 cm.
*Width of sepals.*—0.2–0.3 cm.
*Shape.*—Linear.
*Apex.*—Acute.
*Texture.*—Villous; many glandular hairs, some with an orange hue.
*Color.*—RHS 144A.

Reproductive organs:
*Stamens.*—4–6, sometimes fused to petaloids.
*Filament color.*—RHS 155B but whiter.
*Pollen color.*—RHS 22A.
*Pollen amount.*—Scant.
*Pistil.*—1.
*Pistil length.*—1.0 cm.
*Stigma color.*—RHS 58B.
*Style color.*—RHS N66A.
*Style length.*—0.8 cm.
*Fruit set.*—Not observed.

Disease and insect resistance: Not observed.

Comparison with Known Cultivars

When the instant plant is compared to the female parental cultivar 7886-1, 'Clips Litsaltwo' has greater vigor, a light salmon flower color, and darker green leaves than 7886-1. When 'Clips Litsaltwo' is compared to the male parental cultivar 'Champion', 'Clips Litsaltwo' has greater vigor, a light salmon flower color, and darker green leaves than 'Champion'.

'Clips Litsaltwo' differs from the comparison variety, 'Fisrolisa' (U.S. Plant Pat. No. 13,193) also known as 'Rocky Mountain Light Salmon' by having more petals, a larger flower and the flower bud color is creamy white, whereas the 'Rocky Mountain Light Salmon' flower bud is creamy white with some pink.

I claim:

1. A new and distinct cultivar of *Pelargonium* plant as shown and described herein.

* * * * *